(12) United States Patent
Boukhny et al.

(10) Patent No.: US 8,771,301 B2
(45) Date of Patent: *Jul. 8, 2014

(54) ULTRASONIC HANDPIECE

(75) Inventors: Mikhail Boukhny, Laguna Niguel, CA (US); James Chon, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 670 days.

This patent is subject to a terminal disclaimer.

(21) Appl. No.: 12/558,044

(22) Filed: Sep. 11, 2009

(65) Prior Publication Data

US 2010/0004585 A1    Jan. 7, 2010

Related U.S. Application Data

(63) Continuation of application No. 10/916,675, filed on Aug. 12, 2004, now Pat. No. 7,651,490.

(51) Int. Cl.
*A61B 17/32* (2006.01)

(52) U.S. Cl.
USPC .............................. 606/169; 604/22

(58) Field of Classification Search
USPC ............. 606/128, 159, 169, 170, 171, 180; 600/437, 439, 471; 604/22
See application file for complete search history.

(56) References Cited

U.S. PATENT DOCUMENTS

| | | |
|---|---|---|
| 3,526,219 A | 9/1970 | Balamuth |
| 3,589,363 A | 6/1971 | Banko |
| 3,601,126 A | 8/1971 | Estes et al. |
| 3,693,613 A | 9/1972 | Kelman |
| 3,812,855 A | 5/1974 | Banko |
| 3,812,858 A | 5/1974 | Oringer |
| 3,857,387 A | 12/1974 | Shock |
| 3,902,495 A | 9/1975 | Weiss et al. |
| 3,930,505 A | 1/1976 | Wallach |
| 3,942,519 A | 3/1976 | Shock |
| 3,952,732 A | 4/1976 | Shock |
| 3,956,826 A | 5/1976 | Perdreaux, Jr. |
| 3,964,487 A | 6/1976 | Judson |
| 3,990,452 A | 11/1976 | Murry et al. |

(Continued)

FOREIGN PATENT DOCUMENTS

| | | |
|---|---|---|
| EP | 359217 | 3/1990 |
| JP | 09009656 | 10/1997 |

(Continued)

OTHER PUBLICATIONS

Jiromaru Tsujino, "Ultrasonic Motor Using a One-Dimensional Longitudinal-Torsional Vibration Converter with Diagonal Slits", Smart Mater. Struct. 7 (1998), pp. 345-351.

(Continued)

*Primary Examiner* — Dianne Dornbusch
(74) *Attorney, Agent, or Firm* — Kenneth D. Bassinger

(57) ABSTRACT

A handpiece having a single set of piezoelectric elements polarized to produce longitudinal motion when excited at the relevant resonant frequency. The piezoelectric crystals are connected to an ultrasonic horn to which a cutting tip is attached. The horn and/or the cutting tip contains a plurality of diagonal slits or grooves. The slits or grooves produce optimized torsional movement in the cutting tip when the piezoelectric crystals are excited at a second resonant frequency. Preferably, the two drive frequencies are not coincident, but provided in non-overlapping pulses.

20 Claims, 2 Drawing Sheets

(56) References Cited

U.S. PATENT DOCUMENTS

| | | |
|---|---|---|
| 4,024,467 A | 5/1977 | Andrews et al. |
| 4,024,866 A | 5/1977 | Wallach |
| 4,114,623 A | 9/1978 | Meinke et al. |
| 4,126,137 A | 11/1978 | Archibald |
| 4,156,187 A | 5/1979 | Murry et al. |
| 4,168,707 A | 9/1979 | Douvas et al. |
| 4,184,510 A | 1/1980 | Murry et al. |
| 4,223,676 A | 9/1980 | Wuchinich |
| 4,246,902 A | 1/1981 | Martinez |
| 4,248,232 A | 2/1981 | Engelbrecht et al. |
| 4,406,284 A | 9/1983 | Banko |
| 4,417,578 A | 11/1983 | Banko |
| 4,493,694 A | 1/1985 | Wuchinich |
| 4,496,342 A | 1/1985 | Banko |
| 4,504,264 A | 3/1985 | Kelman |
| 4,508,532 A | 4/1985 | Drews et al. |
| 4,515,583 A | 5/1985 | Sorich |
| 4,589,415 A | 5/1986 | Haaga |
| 4,590,935 A | 5/1986 | Ranalli |
| 4,609,368 A | 9/1986 | Dotson, Jr. |
| 4,651,280 A | 3/1987 | Chang et al. |
| 4,658,819 A | 4/1987 | Harris et al. |
| 4,705,500 A | 11/1987 | Reimels et al. |
| 4,712,544 A | 12/1987 | Ensslin |
| 4,739,759 A | 4/1988 | Rexroth et al. |
| 4,750,488 A | 6/1988 | Wuchinich et al. |
| 4,770,654 A | 9/1988 | Rogers et al. |
| 4,793,346 A | 12/1988 | Mindich |
| 4,827,911 A | 5/1989 | Broadwin et al. |
| 4,869,715 A | 9/1989 | Sherburne |
| 4,922,902 A | 5/1990 | Wuchinich et al. |
| 4,961,424 A | 10/1990 | Kubota et al. |
| 4,969,885 A | 11/1990 | Farin |
| 4,989,583 A | 2/1991 | Hood |
| 4,989,588 A | 2/1991 | Kubota et al. |
| 5,026,387 A | 6/1991 | Thomas |
| 5,116,343 A * | 5/1992 | Ams et al. .................... 606/128 |
| 5,139,509 A | 8/1992 | Fischer et al. |
| 5,151,085 A | 9/1992 | Sakurai et al. |
| 5,154,694 A | 10/1992 | Kelman |
| 5,154,696 A | 10/1992 | Shearing |
| 5,160,317 A | 11/1992 | Costin |
| 5,180,363 A | 1/1993 | Idemoto et al. |
| 5,188,102 A | 2/1993 | Idemoto et al. |
| 5,205,817 A | 4/1993 | Idemoto et al. |
| 5,222,959 A | 6/1993 | Anis |
| 5,242,385 A | 9/1993 | Strukel |
| 5,279,547 A | 1/1994 | Costin |
| 5,304,115 A | 4/1994 | Pflueger et al. |
| 5,342,293 A | 8/1994 | Zanger |
| 5,359,996 A | 11/1994 | Hood |
| 5,431,664 A | 7/1995 | Ureche et al. |
| 5,520,633 A | 5/1996 | Costin |
| 5,569,188 A | 10/1996 | Mackool |
| 5,591,127 A | 1/1997 | Barwick, Jr. et al. |
| 5,676,649 A | 10/1997 | Boukhny et al. |
| 5,700,240 A | 12/1997 | Barwick, Jr. et al. |
| 5,722,945 A | 3/1998 | Anis et al. |
| 5,733,256 A | 3/1998 | Costin |
| 5,766,146 A | 6/1998 | Barwick, Jr. |
| 5,808,396 A | 9/1998 | Boukhny |
| 5,865,790 A | 2/1999 | Bair |
| 6,027,515 A | 2/2000 | Cimino |
| 6,028,387 A | 2/2000 | Boukhny |
| 6,077,285 A | 6/2000 | Boukhny |
| 6,083,193 A | 7/2000 | Kadziauskas et al. |
| 6,175,180 B1 | 1/2001 | Angelini et al. |
| 6,179,808 B1 | 1/2001 | Boukhny et al. |
| 6,193,683 B1 | 2/2001 | Ludin et al. |
| 6,261,283 B1 | 7/2001 | Morgan et al. |
| 6,261,297 B1 | 7/2001 | Kadziauskas et al. |
| 6,283,974 B1 | 9/2001 | Alexander |
| 6,315,755 B1 | 11/2001 | Sussman |
| 6,402,769 B1 | 6/2002 | Boukhny |
| 6,629,948 B2 | 10/2003 | Rockley et al. |
| 6,699,212 B1 | 3/2004 | Kadziauskas et al. |
| 6,780,165 B2 | 8/2004 | Kadziauskas et al. |
| 7,374,552 B2 | 5/2008 | Wuchinich |
| 2001/0001123 A1 | 5/2001 | Madan et al. |
| 2001/0011176 A1 * | 8/2001 | Boukhny ..................... 606/169 |
| 2003/0045887 A1 * | 3/2003 | Sakurai et al. ............... 606/128 |
| 2003/0164659 A1 | 9/2003 | Iino et al. |
| 2004/0092800 A1 | 5/2004 | MacKool |
| 2004/0092922 A1 | 5/2004 | Kadziauskas et al. |
| 2004/0215127 A1 | 10/2004 | Kadziauskas et al. |
| 2006/0041200 A1 | 2/2006 | Dotter et al. |

FOREIGN PATENT DOCUMENTS

| | | |
|---|---|---|
| JP | 2003033364 | 4/2003 |
| WO | WO 8705793 | 10/1987 |
| WO | WO 92/07622 | 5/1992 |
| WO | WO 99/45868 | 9/1999 |
| WO | WO 01/41672 | 6/2001 |
| WO | WO 2004/080505 | 9/2004 |

OTHER PUBLICATIONS

Shuyu, Lin, "Sandwiched Piezoelectric Ultrasonic Transducers of Longitudinal-Torsional Compound Vibratiion Modes." IEEE Transactions of Ultrasonicas, Ferroelectics and Frequency Control, Nov. 1997; Pg.

* cited by examiner

ULTRASONIC HANDPIECE

This application is a continuation of U.S. patent application Ser. No. 10/916,675, filed Aug. 12, 2004, now U.S. Pat. No. 7,651,490, issued Jan. 26, 2010.

BACKGROUND OF THE INVENTION

This invention relates to ultrasonic devices and more particularly to devices for tuning and controlling an ophthalmic phacoemulsification handpiece.

A typical ultrasonic surgical device suitable for ophthalmic procedures consists of an ultrasonically driven handpiece, an attached hollow cutting tip, an irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece at its nodal points by relatively inflexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve. Ultrasonic handpieces and cutting tips are more fully described in U.S. Pat. Nos. 3,589,363; 4,223,676; 4,246,902; 4,493,694; 4,515,583; 4,589,415; 4,609,368; 4,869,715; and 4,922,902, the entire contents of which are incorporated herein by reference.

When used to perform phacoemulsification, the ends of the cutting tip and irrigating sleeve are inserted into a small incision of predetermined width in the cornea, sclera, or other location in the eye tissue in order to gain access to the anterior chamber of the eye. The cutting tip is ultrasonically vibrated along its longitudinal axis within the irrigating sleeve by the crystal-driven ultrasonic horn, thereby emulsifying upon contact the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the bore of the cutting tip, the horn bore, and the aspiration line and into a collection device. The aspiration of emulsified tissue is aided by a saline flushing solution or irrigant that is injected into the surgical site through the small annular gap between the inside surface of the irrigating sleeve and the outside surface of the cutting tip.

There have been prior attempts to combine ultrasonic longitudinal motion of the cutting tip with rotational motion of the tip, see U.S. Pat. No. 5,222,959 (Anis), U.S. Pat. No. 5,722,945 (Anis, et al.) and U.S. Pat. No. 4,504,264 (Kelman), the entire contents of which are incorporated herein by reference. These prior attempts have used electric motors to provide the rotation of the tip which require O-ring or other seals that can fail in addition to the added complexity and possible failure of the motors.

There have also been prior attempts to generate both longitudinal and torsional motion without the use of electric motors. For example, in U.S. Pat. Nos. 6,028,387, 6,077,285 and 6,402,769 (Boukhny), one of the inventors of the current invention, describes a handpiece having two pairs of piezoelectric crystals are used. One pair is polarized to product longitudinal motion. The other pair is polarized to produce torsional motion. Two separate drive signals are used to drive the two pairs of crystals. In actual practice, making a handpiece using two pairs of crystals resonate in both longitudinal and torsional directions is difficult to achieve. One possible solution, also described by one of the current inventors, is described in U.S. Patent Publication No. US 2001/0011176 A1 (Boukhny). This reference discloses a handpiece have a single set of piezoelectric crystals that produces longitudinal motion, and a series of diagonal slits on the handpiece horn or tip that produce torsional motion when the horn or tip is driven at the resonate frequency of the piezoelectric crystals. Again, in practice, the resonate frequency of the piezoelectric crystals and the tip or horn did not coincide, so simultaneous longitudinal and torsional motion was difficult to achieve.

Accordingly, a need continues to exist for a reliable ultrasonic handpiece that will vibrate both longitudinally and torsionally, either simultaneously or separately.

BRIEF SUMMARY OF THE INVENTION

The present invention improves upon prior art ultrasonic handpieces by providing a handpiece having a single set of piezoelectric elements polarized to produce longitudinal motion when excited at the relevant resonant frequency. The piezoelectric crystals are connected to an ultrasonic horn to which a cutting tip is attached. The horn and/or the cutting tip contains a plurality of diagonal slits or grooves. The slits or grooves produce optimized torsional movement in the cutting tip when the piezoelectric crystals are excited at a second resonant frequency. Preferably, the two drive frequencies are not coincident, but provided in non-overlapping pulses.

It is accordingly an object of the present invention to provide an ultrasound handpiece having both longitudinal and torsional motion.

It is a further object of the present invention to provide an ultrasound handpiece with a horn having a series of diagonal slits to produce torsional motion.

Other objects, features and advantages of the present invention will become apparent with reference to the drawings, and the following description of the drawings and claims.

DETAILED DESCRIPTION OF THE INVENTION

Figure 1:
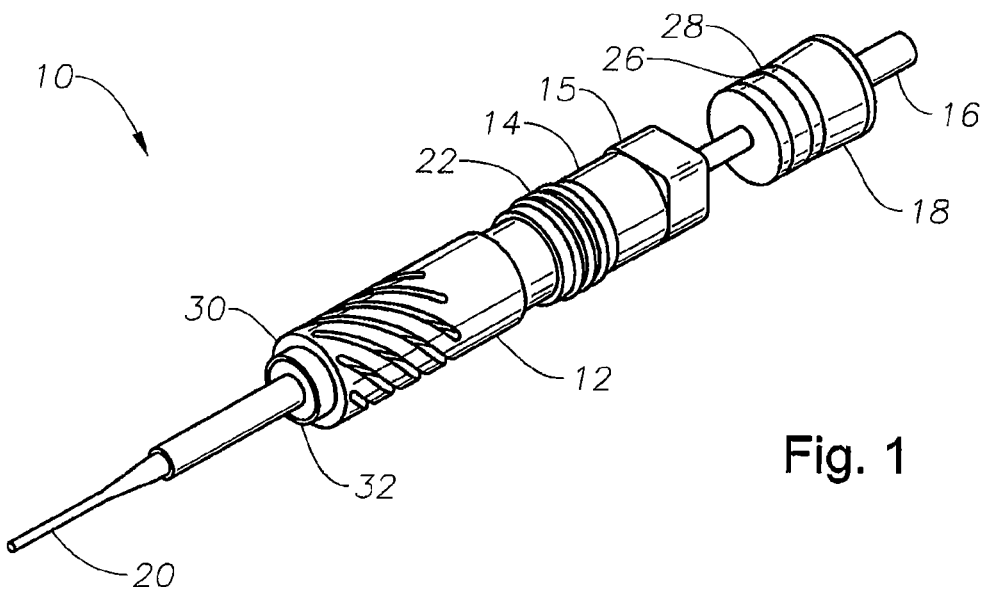
FIG. 1 is a perspective view of the handpiece of the present invention with the outer case removed.

As best seen in FIG. 1 handpiece 10 of the present invention generally comprises ultrasonic horn 12, typically made from a titanium alloy. Horn 12 has a plurality of helical slits, which will be discussed below. A plurality (typically 1 or 2 pairs) of ring-shaped piezoelectric elements 14 are held by compression nut 15 against horn 12. Aspiration shaft 16 extends down the length of handpiece 10 through horn 12, piezoelectric elements 14, nut 15 and through plug 18 at the distal end of handpiece 10. Aspiration tube 16 allows material to be aspirated through hollow tip 20, which is attached to horn 12, and through and out handpiece 10. Plug 18 seals outer shell 11 of handpiece 10 fluid tight, allowing handpiece 10 to be autoclaved without adversely affecting piezoelectric elements 14. Additional grooves 22 for sealing O-ring gaskets (not shown) are provided on horn 12.

Figure 2:
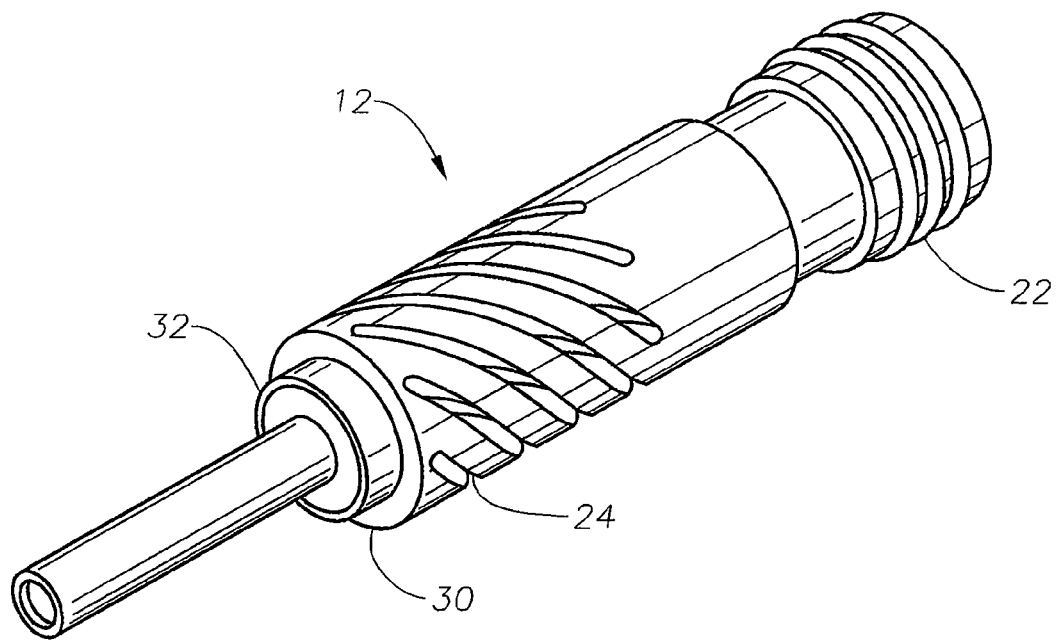
FIG. 2 is a perspective view of the ultrasonic horn that may be used with the handpiece of the present invention.

As best seen in FIG. 2, horn 12 contains a plurality of spiral slits 24. Preferably, the width of slits 24 is between 2% and 65% of the outside diameter of horn 12. This, of course, will affect how many slits 24 can be made on horn 12 (e.g., if slits 24 are 65% of the diameter of horn 12, then only one slit 24 may be cut into horn 12). The width of slits 24 selected will depend upon the desired amount of torsional movement. The depth of slits 24 in horn 12 preferably is between 4% and 45% of the outside diameter of horn 12. Slits 24 may have a flat or square cut bottom, but preferably have a rounded or radiused bottom, which are easier to manufacture. The length of slits 24 preferably is between 8% and 75% of the length of the larger diameter of horn 12. The pitch of slits 24 preferably is between 125% and 500% of the larger diameter of horn 12. By way of example, the inventors have found that one suitable configuration of slits 24 on horn 12 with an outside diameter of 0.475 inches is a total of eight slits 24, having a width of 0.04 inches, a depth of 0.140 (with a full radius bottom), a length of 0.7 inches and a pitch of 1.35 inches gives suitable torsional movement of horn 12 without compromising the longitudinal movement of horn 12.

As best seen in FIG. 1, the location of longitudinal and torsional nodal points (the points with zero velocity of the respective mode) is important for proper functioning of handpiece 10. The torsional node 26 preferably is located at the proximal longitudinal node 28, so that the torsional node 26 and the longitudinal node 28 are coincident, e.g., both of which are located on plug 18. Handpiece 10 also contains a distal longitudinal node 30 located at reduced diameter portion 32 of horn 12.

Figure 3:
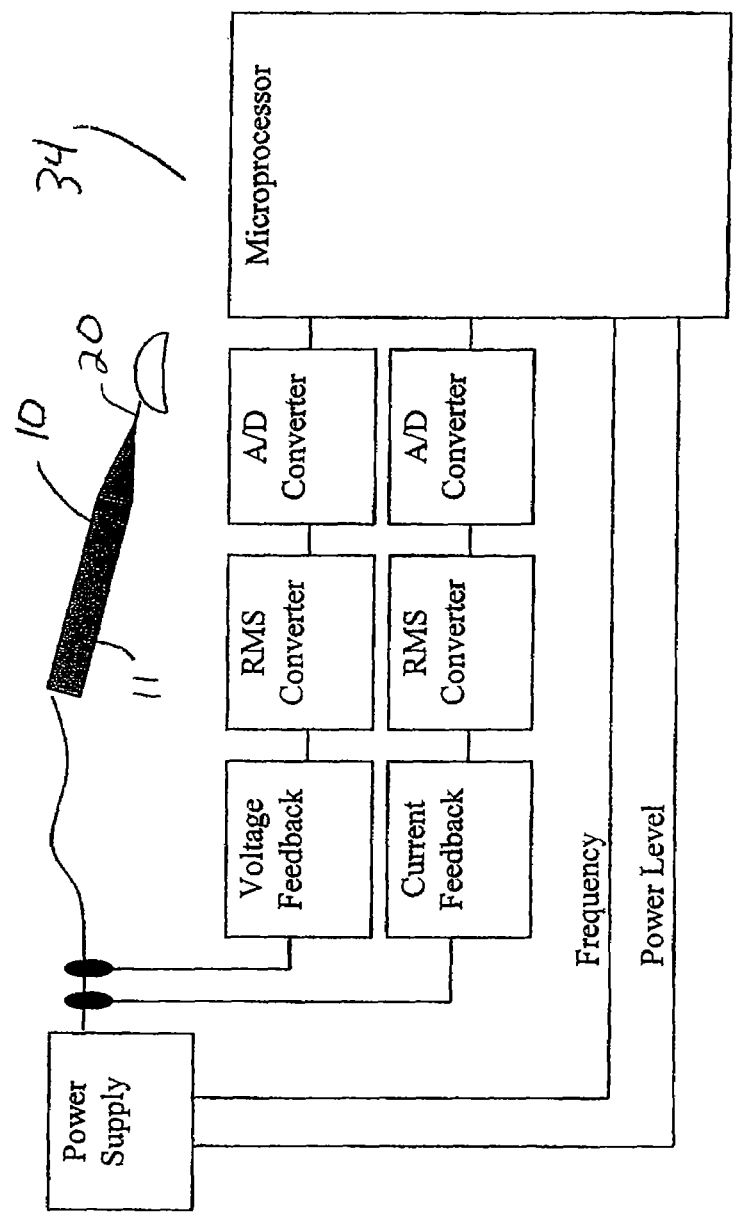
FIG. 3 a block diagram of a driving circuit that may be used with the present invention.

As best seen in FIG. 3, drive circuit 34 that may be used with handpiece 10 of the present invention preferably is similar to that described in U.S. Pat. No. 5,431,664, the entire contents of which being incorporated herein by reference, in that drive circuit 34 tracks admittance of handpiece 10 and controls the frequency of handpiece 10 to maintain a constant admittance. However, drive circuit 34 monitors both the torsional mode and the longitudinal mode and controls these modes in handpiece 10 using two different drive frequencies. Preferably, the torsional drive signal is approximately 32 kHz and the longitudinal drive signal is 44 kHz, but these frequencies will change depending upon the piezoelectric elements 14 used and the size and shape of horn 12 and slits 24. Although both the longitudinal or the torsional drive signal may be supplied in a continuous manner, preferably the longitudinal drive signal and the torsion drive signal are alternated, so that the drive signal is provided in a desired pulse at one frequency and then switched to the other frequency for a similar pulse, with no overlap between the two frequencies, but no gap or pause in the drive signal. Alternatively, the drive signal can be operated in a similar manner as described, but short pauses or gaps in the drive signal can be introduced. In addition, the amplitude of the drive signal can be modulated and set independently for each frequency.

While certain embodiments of the present invention have been described above, these descriptions are given for purposes of illustration and explanation. Variations, changes, modifications and departures from the systems and methods disclosed above may be adopted without departure from the scope or spirit of the present invention.

What is claimed is:

1. An ultrasonic hand piece, comprising:
   a shell; and
   an ultrasonic horn held within the shell, the horn configured to produce torsional movement of a cutting tip in response to a drive signal having a first frequency and longitudinal movement of the cutting tip in response to a drive signal having a second frequency;
   wherein the horn is held within the shell so that a torsional nodal point and a proximal longitudinal nodal point are coincident at a plug that seals the shell on an end of the hand piece opposite the cutting tip.

2. The apparatus of claim 1 wherein the first drive signal and the second drive signal are alternated and do not overlap.

3. The hand piece of claim 1 further comprising:
   an aspiration shaft extending through the horn.

4. The hand piece of claim 1 wherein the cutting tip is fluidly coupled to an aspiration shaft.

5. The hand piece of claim 1 further comprising:
   a drive circuit for driving the hand piece.

6. The hand piece of claim 1 wherein the first frequency is about 32 kHz.

7. The hand piece of claim 1 wherein the second frequency is about 44 kHz.

8. An ultrasonic hand piece comprising:
   a shell having proximal and distal ends;
   a cutting tip located at a distal end of the shell;
   a plug located at a proximal end of the shell, the plug sealing the shell;
   an ultrasonic horn at least partially located in the shell, the horn producing torsional movement in the cutting tip in response to a drive signal having a first frequency and longitudinal movement in the cutting tip in response to a drive signal having a second frequency; and
   a piezoelectric element coupled to the horn;
   wherein a torsional nodal point and a longitudinal nodal point are coincident at the plug.

9. The hand piece of claim 8 further comprising:
   an aspiration shaft extending through the horn.

10. The hand piece of claim 9 the cutting tip is fluidly coupled to the aspiration shaft.

11. The hand piece of claim 8 further comprising:
    a drive circuit for driving the hand piece.

12. The hand piece of claim 8 wherein the first frequency is about 32 kHz.

13. The hand piece of claim 8 wherein the second frequency is about 44 kHz.

14. An ultrasonic hand piece comprising:
    a shell with proximal and distal ends;
    a plug located at the proximal end of the shell;
    a cutting tip located at a distal end of the shell; and
    an ultrasonic horn at least partially located in the shell and coupled to the shell at the proximal end, the horn producing torsional movement in the cutting tip in response to a drive signal having a first frequency and longitudinal movement in the cutting tip in response to a drive signal having a second frequency;
    wherein a torsional nodal point and a longitudinal nodal point are coincident at the proximal end of the shell.

15. The hand piece of claim 14 wherein the horn is sealed to the shell at the proximal end of the shell.

16. A phacoemulsification hand piece comprising:
    a shell;

a horn with proximal and distal ends, the horn at least partially located in the shell;
a tip coupled to the distal end of the horn;
a plug located on a proximal end of the horn, the plug sealing the horn to the shell;
wherein the horn produces torsional movement in the tip in response to a drive signal having a first frequency and longitudinal movement in the tip in response to a drive signal having a second frequency, and further wherein a torsional nodal point and a longitudinal nodal point are coincident at the proximal end of the horn.

17. The hand piece of claim 16 further comprising:
an aspiration shaft extending through the horn.

18. The hand piece of claim 16 further comprising:
a drive circuit for driving the piezoelectric element.

19. A phacoemulsification hand piece comprising:
a shell;
a horn having proximal and distal ends, the horn at least partially located in the shell, the horn producing torsional movement at a distal end of the horn in response to a drive signal having a first frequency and longitudinal movement at a distal end of the horn in response to a drive signal having a second frequency; and
a plug located near the proximal end of the horn, the plug for sealing the shell;
wherein a torsional nodal point and a longitudinal nodal point are coincident at the proximal end of the horn, the proximal end of the horn opposite a cutting tip.

20. A phacoemulsification hand piece comprising:
a shell configured to be held in the hand;
a horn having proximal and distal ends, the horn at least partially located in the shell, the horn producing torsional movement at a distal end of the horn in response to a drive signal having a first frequency and longitudinal movement at a distal end of the horn in response to a drive signal having a second frequency;
a cutting tip coupled to the horn, the cutting tip for insertion into an eye, the cutting tip configured to remove a lens from the eye when the cutting tip is vibrated;
an aspiration shaft extending through the horn;
a piezoelectric element coupled to the horn; and
a plug located near the proximal end of the horn, the plug for sealing the shell;
wherein a torsional nodal point and a longitudinal nodal point are coincident at the plug.

* * * * *